United States Patent [19]

Maloy et al.

[11] Patent Number: 5,424,290
[45] Date of Patent: Jun. 13, 1995

[54] BIOLOGICALLY ACTIVE PEPTIDES AND USES THEREFOR

[75] Inventors: W. Lee Maloy; U. Prasad Kari, both of Lansdale, Pa.

[73] Assignee: Magainin Pharmaceuticals Inc., Plymouth Meeting, Pa.

[21] Appl. No.: 965,663

[22] Filed: Oct. 26, 1992

[51] Int. Cl.$^6$ .................... A61K 38/00; C07K 14/00; C07K 14/005

[52] U.S. Cl. .......................... 514/13; 514/12; 530/324; 530/325; 530/326

[58] Field of Search .................... 514/12, 13; 530/324, 530/325–326

[56] References Cited

U.S. PATENT DOCUMENTS

| | | | |
|---|---|---|---|
| 4,810,777 | 3/1989 | Zasloff | 530/324 |
| 4,962,277 | 10/1990 | Cueruo et al. | 514/14 |
| 5,114,921 | 5/1992 | Zasloff | 514/12 |

FOREIGN PATENT DOCUMENTS

| | | |
|---|---|---|
| 8806597 | 9/1988 | WIPO . |
| 9100869 | 1/1991 | WIPO . |
| 9112015 | 8/1991 | WIPO . |

OTHER PUBLICATIONS

Christensen, *Proc. Natl. Acad. Sci.*, vol. 85, pp. 5072–5076, 1988.

*Primary Examiner*—Jill Warden
*Assistant Examiner*—S. G. Marshall
*Attorney, Agent, or Firm*—Finnegan, Henderson, Farabow, Garrett & Dunner

[57] ABSTRACT

Novel biologically active amphiphilic peptides having from 21 to 26 amino acid residues, and which may be employed as for inhibiting the growth of target cells, viruses and virally-infected cells.

38 Claims, No Drawings

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note="May be a C-terminal amide, and/

( x i ) SEQUENCE DESCRIPTION: SEQ ID NO:1:

```
Ile Gly Lys Phe Leu Lys Lys Ala Lys Lys Phe Gly Lys Ala Phe Val
 1               5                  10                  15
Lys Ile Leu Lys Lys
            20
```

( 2 ) INFORMATION FOR SEQ ID NO:2:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( D ) OTHER INFORMATION: /note="May be a C-terminal amide, and/

( x i ) SEQUENCE DESCRIPTION: SEQ ID NO:2:

Ile  Lys  Lys  Phe  Leu  Lys  Lys  Ala  Lys  Lys  Phe  Gly  Lys  Lys  Phe  Lys
   1                 5                           10                          15

Lys  Ile  Leu  Lys  Lys
                  20

( 2 ) INFORMATION FOR SEQ ID NO:3:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( D ) OTHER INFORMATION: /note="May be a C-terminal amide, and/

( x i ) SEQUENCE DESCRIPTION: SEQ ID NO:3:

Ile  Gly  Lys  Phe  Leu  Lys  Lys  Ala  Lys  Lys  Phe  Gly  Lys  Lys  Phe  Lys
   1                 5                           10                          15

Lys  Glu  Ile  Lys  Lys
                  20

( 2 ) INFORMATION FOR SEQ ID NO:4:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( D ) OTHER INFORMATION: /note="May be a C-terminal amide, and/

( x i ) SEQUENCE DESCRIPTION: SEQ ID NO:4:

Gly  Ile  Gly  Lys  Ile  Leu  Lys  Lys  Ala  Lys  Lys  Ile  Gly  Lys  Ala  Ile
   1                 5                           10                          15

Val  Lys  Ile  Leu  Lys  Lys
                  20

( 2 ) INFORMATION FOR SEQ ID NO:5:

( i ) SEQUENCE CHARACTERISTICS:
      ( A ) LENGTH: 22 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: one-of(2, 5, 12, 16, 19)
      ( D ) OTHER INFORMATION: /note="May be a C-terminal amide,
         and/or may be acetylated at N-terminus. Xaa is norleucine."

(xi) SEQUENCE DESCRIPTION: SEQ ID NO:5:

```
Gly  Xaa  Gly  Lys  Xaa  Leu  Lys  Lys  Ala  Lys  Lys  Xaa  Gly  Lys  Ala
1                  5                        10                       15

Xaa  Val  Lys  Xaa  Leu  Lys  Lys
                20
```

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note="May be a C-terminal amide, and/

(xi) SEQUENCE DESCRIPTION: SEQ ID NO:6:

```
Gly  Ile  Gly  Lys  Phe  Leu  Lys  Lys  Ala  Lys  Lys  Phe  Gly  Lys  Ala  Phe
1                  5                        10                       15

Val  Lys  Ile  Val  Lys  Lys
                20
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 20
        (D) OTHER INFORMATION: /note="May be a C-terminal amide,
            and/or may be acetylated at N-terminus. Xaa is
            norleucine."

(xi) SEQUENCE DESCRIPTION: SEQ ID NO:7:

```
Gly  Ile  Gly  Lys  Phe  Leu  Lys  Lys  Ala  Lys  Lys  Phe  Gly  Lys  Ala  Phe
1                  5                        10                       15

Val  Lys  Ile  Xaa  Lys  Lys
                20
```

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note="May be a C-terminal amide, and/

(xi) SEQUENCE DESCRIPTION: SEQ ID NO:8:

```
Gly  Ile  Gly  Lys  Phe  Leu  Lys  Lys  Ala  Lys  Lys  Phe  Gly  Lys  Ala  Phe
1                  5                        10                       15

Val  Lys  Ile  Leu  Lys  Lys  Arg
                20
```

(2) INFORMATION FOR SEQ ID NO:9:

( i ) SEQUENCE CHARACTERISTICS:
   ( A ) LENGTH: 23 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( D ) OTHER INFORMATION: /note="May be a C-terminal amide, and/

( x i ) SEQUENCE DESCRIPTION: SEQ ID NO:9:

Gly Ile Gly Lys Phe Leu Lys Lys Ala Lys Lys Phe Gly Lys Ala Phe
1               5                   10                  15

Val Lys Ile Leu Lys Lys Asn
            20

( 2 ) INFORMATION FOR SEQ ID NO:10:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 23
      ( D ) OTHER INFORMATION: /note="May be a C-terminal amide,
             and/or may be acetylated at N-terminus. Xaa is
             homoserine."

( x i ) SEQUENCE DESCRIPTION: SEQ ID NO:10:

Gly Ile Gly Lys Phe Leu Lys Lys Ala Lys Lys Phe Gly Lys Ala Phe
1               5                   10                  15

Val Lys Ile Leu Lys Lys Xaa
            20

( 2 ) INFORMATION FOR SEQ ID NO:11:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( D ) OTHER INFORMATION: /note="May be a C-terminal amide, and/

( x i ) SEQUENCE DESCRIPTION: SEQ ID NO:11:

Met Gly Ile Gly Lys Phe Leu Lys Lys Ala Lys Lys Phe Gly Lys Ala
1               5                   10                  15

Phe Val Lys Ile Leu Lys Lys
            20

( 2 ) INFORMATION FOR SEQ ID NO:12:

( i ) SEQUENCE CHARACTERISTICS:
      ( A ) LENGTH: 24 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( D ) OTHER INFORMATION: /note="May be a C-terminal amide, and/

( x i ) SEQUENCE DESCRIPTION: SEQ ID NO:12:

Arg Arg Gly Ile Gly Lys Phe Leu Lys Lys Ala Lys Lys Phe Gly Lys
1               5                   10                  15

Ala Phe Val Lys Ile Leu Lys Lys
            20

( 2 ) INFORMATION FOR SEQ ID NO:13:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note="May be a C-terminal amide, and/

( x i ) SEQUENCE DESCRIPTION: SEQ ID NO:13:

Arg Arg Gly Ile Gly Lys Phe Leu Lys Lys Ala Lys Lys Phe Gly Lys
1               5                   10                  15

Ala Phe Val Lys Ile Leu Lys Lys Gly
            20                  25

( 2 ) INFORMATION FOR SEQ ID NO:14:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note="May be a C-terminal amide, and/

( x i ) SEQUENCE DESCRIPTION: SEQ ID NO:14:

Gly Ile Gly Lys Phe Leu Lys Lys Ala Lys Lys Phe Gly Lys Ala Phe
1               5                   10                  15

Val Lys Ile Leu Lys Lys Asp Asp Lys
            20                  25

( 2 ) INFORMATION FOR SEQ ID NO:15:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note="May be a C-terminal amide, and/

( x i ) SEQUENCE DESCRIPTION: SEQ ID NO:15:

Gly Ile Gly Lys Phe Leu Lys Lys Ala Lys Lys Phe Gly Lys Ala Phe
1               5                   10                  15

Val Lys Ile Leu Lys Lys Ile Glu Gly Arg
            20                  25

( 2 ) INFORMATION FOR SEQ ID NO:16:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( D ) OTHER INFORMATION: /note="May be a C-terminal amide, and/

( x i ) SEQUENCE DESCRIPTION: SEQ ID NO:16:

```
Gly Ile Ile Gly Lys Phe Leu Lys Lys Ala Lys Lys Phe Gly Lys Ala
1               5                   10                  15

Phe Val Lys Ile Leu Lys Lys
            20
```

( 2 ) INFORMATION FOR SEQ ID NO:17:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( D ) OTHER INFORMATION: /note="May be a C-terminal amide, and/

( x i ) SEQUENCE DESCRIPTION: SEQ ID NO:17:

```
Gly Ile Gly Lys Phe Leu Lys Leu Ala Lys Lys Phe Ala Lys Gly Phe
1               5                   10                  15

Lys Lys Ile Leu Lys Lys
            20
```

( 2 ) INFORMATION FOR SEQ ID NO:18:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( D ) OTHER INFORMATION: /note="May be a C-terminal amide, and/

( x i ) SEQUENCE DESCRIPTION: SEQ ID NO:18:

```
Gly Ile Gly Lys Phe Leu Lys Lys Ala Lys Lys Gly Ile Gly Ala Val
1               5                   10                  15

Leu Lys Val Leu Thr Thr Gly Lys
            20
```

( 2 ) INFORMATION FOR SEQ ID NO:19:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( D ) OTHER INFORMATION: /note="May be a C-terminal amide, and/

( x i ) SEQUENCE DESCRIPTION: SEQ ID NO:19:

```
Gly Ile Gly Lys Phe Leu Lys Lys Ala Lys Lys Phe Gly Lys Ala Phe
1               5                   10                  15

Ile Lys Ile Leu Lys Lys
                20
```

( 2 ) INFORMATION FOR SEQ ID NO:20:

( i ) SEQUENCE CHARACTERISTICS:
- ( A ) LENGTH: 22 amino acids
- ( B ) TYPE: amino acid
- ( C ) STRANDEDNESS: single
- ( D ) TOPOLOGY: linear ( i i ) MOLECULE TYPE: peptide ( i x ) FEATURE:
- ( A ) NAME/KEY: Modified-site
- ( B ) LOCATION: 14
- ( D ) OTHER INFORMATION: /note="May be a C-terminal amide, and/or may be acetylated at N-terminus. Xaa is homoarginine."

( x i ) SEQUENCE DESCRIPTION: SEQ ID NO:20:

Gly Ile Gly Lys Phe Leu Lys Lys Ala Lys Lys Phe Gly Xaa Ala Phe
1               5                   10                  15

Val Lys Ile Leu Lys Lys
            20

( 2 ) INFORMATION FOR SEQ ID NO:21:

( i ) SEQUENCE CHARACTERISTICS:
- ( A ) LENGTH: 22 amino acids
- ( B ) TYPE: amino acid
- ( C ) STRANDEDNESS: single
- ( D ) TOPOLOGY: linear ( i i ) MOLECULE TYPE: peptide ( i x ) FEATURE:
- ( A ) NAME/KEY: Modified-site
- ( B ) LOCATION: 22
- ( D ) OTHER INFORMATION: /note="May be a C-terminal amide, and/or may be acetylated at N-terminus. Xaa is homoserine."

( x i ) SEQUENCE DESCRIPTION: SEQ ID NO:21:

Gly Ile Gly Lys Phe Leu Lys Lys Ala Lys Lys Phe Gly Lys Ala Phe
1               5                   10                  15

Val Lys Ile Leu Lys Xaa
            20

( 2 ) INFORMATION FOR SEQ ID NO:22:

( i ) SEQUENCE CHARACTERISTICS:
- ( A ) LENGTH: 21 amino acids
- ( B ) TYPE: amino acid
- ( C ) STRANDEDNESS: single
- ( D ) TOPOLOGY: linear ( i i ) MOLECULE TYPE: peptide ( i x ) FEATURE:
- ( D ) OTHER INFORMATION: /note="May be a C-terminal amide, and/

( x i ) SEQUENCE DESCRIPTION: SEQ ID NO:22:

Gly Gly Lys Phe Leu Lys Lys Ala Lys Lys Phe Gly Lys Ala Phe Val
1               5                   10                  15

Lys Ile Leu Lys Lys
            20

( 2 ) INFORMATION FOR SEQ ID NO:23:

( i ) SEQUENCE CHARACTERISTICS:
- ( A ) LENGTH: 21 amino acids
- ( B ) TYPE: amino acid
- ( C ) STRANDEDNESS: single
- ( D ) TOPOLOGY: linear ( i i ) MOLECULE TYPE: peptide ( x i ) SEQUENCE DESCRIPTION: SEQ ID NO:23:

Phe Gly Lys Ile Leu Lys Lys Ala Lys Lys Ile Gly Lys Ala Ile Val
1               5                   10                  15

Lys Phe Leu Lys Lys
            20

BIOLOGICALLY ACTIVE PEPTIDES AND USES THEREFOR

This invention relates to biologically active peptides. More particularly, this invention relates to novel biologically active peptides for inhibiting the growth of target cells, viruses, and virally-infected cells.

In accordance with an aspect of the present invention, there is provided a peptide having the following structural formula:

Ile $R_1$ Lys Phe Leu Lys Lys Ala Lys Lys Phe
                5                        10

Gly Lys $R_2$ Phe $R_3$ Lys $R_4$ $R_5$ Lys Lys,
            15                    20 wherein $R_1$ is Gly or Lys; $R_2$ is Ala or Lys; $R_3$ is Val or Lys; $R_4$ is Ile or Glu; and $R_5$ is Leu or Ile.

In one embodiment, the peptide has the following structural formula:

Ile Gly Lys Phe Leu Lys Lys Ala Lys Lys Phe
                5                        10

Gly Lys Ala Phe Val Lys Ile Leu Lys Lys
            15                  20

(SEQ ID NO: 1).

In another embodiment, the peptide has the following structural formula:

Ile Lys Lys Phe Leu Lys Lys Ala Lys Lys
                5                10

Phe Gly Lys Lys Phe Lys Lys Ile Leu Lys Lys.
            15                        20

(SEQ ID NO: 2).

In yet another embodiment, the peptide has the following structural formula:

Ile Gly Lys Phe Leu Lys Lys Ala Lys Lys
                5                10

Phe Gly Lys Lys Phe Lys Lys Glu Ile Lys Lys
            15                        20

(SEQ ID NO: 3).

In accordance with another aspect of the present invention, there is provided a peptide having the following structural formula:

Gly $R_1$ Gly Lys $R_2$ Leu Lys Lys Ala Lys Lys
                5                        10

$R_3$ Gly Lys Ala $R_4$ Val Lys $R_5$ Leu Lys Lys,
            15                        20 wherein each of $R_1$, $R_2$, $R_3$, $R_4$ and $R_5$ is Ile or norleucine.

In one embodiment, each of $R_1$, $R_2$, $R_3$, $R_4$ and $R_5$ is Ile, and such a peptide has the following structural formula:

Gly Ile Glu Lys Ile Leu Lys Lys Ala Lys
                5                        10

Lys Ile Gly Lys Ala Ile Val Lys Ile Leu
            15                        20

Lys Lys (SEQ ID NO: 4).

In another embodiment, each of $R_1$, $R_2$, $R_3$, $R_4$ and $R_5$ is norleucine, and such a peptide has the following structural formula:

Gly Xaa Gly Lys Xaa Leu Lys Lys Ala Lys
                5                        10

Lys Xaa Gly Lys Ala Xaa Val Lys Xaa Leu
            15                        20

Lys Lys.

(SEQ ID NO: 5), wherein Xaa is norleucine.

In accordance with another aspect of the present invention, there is provided a peptide having the following structural formula:

Gly Ile Gly Lys Phe Leu Lys Lys Ala Lys
                5                        10

Lys Phe Gly Lys Ala Phe Val Lys Ile R
            15                        20

Lys Lys, wherein R is Val or norleucine.

In one embodiment, R is Val, and the peptide has the following structural formula:
(SEQ ID NO:6).

In another embodiment, R is norleucine and the peptide has the following structural formula:
(SEQ ID NO:7).

In accordance with yet another aspect of the present invention, there is provided a peptide having the following structural formula:

Gly Ile Gly Lys Phe Leu Lys Lys Ala Lys
                5                        10

Lys Phe Gly Lys Ala Phe Val Lys Ile Leu
            15                        20

Lys Lys R, wherein R is Arg, Asn, or homoserine.

In one embodiment, R is Arg, and the peptide has the following structural formula:
(SEQ ID NO:8).

In another embodiment, R is Asn, and the peptide has the following structural formula:
(SEQ ID NO:9)

In another embodiment, R is homoserine, and the peptide has the following structural formula:
(SEQ ID NO:10)

In accordance with a further aspect of the present invention, there is provided a peptide including the following structural formula:

—$R_1$ Gly Ile Gly Lys Phe Leu Lys Lys Ala
                5                        10

Lys Lys Phe Gly Lys Ala Phe Val Lys Ile
            15                        20

Leu Lys Lys-, wherein $R_1$ is Met or Arg.

In one embodiment, $R_1$ is Met, and the peptide has the following structural formula:
(SEQ ID NO:11)
In another embodiment, the peptide includes the following structural formula:

—$R_1$ $R_1$ Gly Ile Gly Lys Phe Leu Lys Lys Ala
                5                                  20

Lys Lys Phe Gly Lys Ala Phe Val Lys
         15                     20

Ile Leu Lys Lys-.

In one embodiment, each $R_1$ is Arg, and the peptide has the following structural formula:
(SEQ ID NO:12).
In another embodiment, the peptide includes the following structural formula:

—$R_1$ $R_1$ Gly Ile Gly Lys Phe Leu Lys Lys
                5                     10

Ala Lys Lys Phe Gly Lys Ala Phe Val Lys
            15                   20

Ile Leu Lys Lys $R_2$-, wherein $R_1$ is Met or Arg, and $R_2$ is hydrophobic amino acid.

The hydrophobic amino acids are Ala, Cys, Phe, Ile, Leu, Met, Gly, Trp, Pro, Tyr, Val, norleucine, and norvaline.

In one embodiment, $R_2$ is Gly, and in a preferred embodiment, each $R_1$ is Arg, and the peptide has the following structural formula:
(SEQ ID NO:13)
In accordance with another aspect of the present invention, there is provided a peptide including the following structural formula:

Gly Ile Gly Lys Phe Leu Lys Lys Ala Lys
        5                     10

Lys Phe Gly Lys Ala Phe Val Lys Ile Leu
         15                   20

Lys Lys, wherein at least one of amino acid residues 15, 21, and 22 is a D-amino acid residue.

In accordance with another aspect of the present invention, there is provided a peptide including the following structural formula:

Gly Ile Gly Lys Phe Leu Lys Lys Ala Lys
        5                     10

Lys Phe Gly Lys Ala Phe Val Lys Ile Leu
         15                   20

Lys Lys $R_1$ $R_2$-, wherein $R_1$ is Asp or Ile, and $R_2$ is Asp or Glu.

In one embodiment, the peptide includes the following structure.

—Gly Ile Gly Lys Phe Leu Lys Lys Ala Lys Lys
         5                   10

Phe Gly Lys Ala Phe Val Lys Ile Leu Lys Lys
          15                20

$R_1$ $R_2$ $R_3$, wherein $R_3$ is a hydrophobic amino acid or a basic hydrophilic amino acid.

The basic hydrophilic amino acids are Lys, Arg, His, ornithine (Orn), homoarginine (Har), 2,4-diaminobutyric acid, and p-aminophenylalanine.

In one embodiment, the peptide has the following structural formula:
(SEQ ID NO:14)
In another embodiment, the peptide includes the following structure:

—Gly Ile Gly Lys Phe Leu Lys Lys Ala Lys Lys
       5                    10

Phe Gly Lys Ala Phe Val Lys Ile Leu
        15                20

Lys Lys $R_1$ $R_2$ $R_3$ $R_4$—, wherein $R_4$ is a basic hydrophilic amino acid.

In one embodiment, the peptide has the following structural formula:
(SEQ ID NO:15).
In accordance with another aspect of the present invention, there is provided a peptide selected from the group consisting of:
(SEQ ID NO:16)
(SEQ ID NO:17)
(SEQ ID NO:18)
(SEQ ID NO:19)
(SEQ ID NO:20)
(SEQ ID NO:21)
(SEQ ID NO:22); and
(SEQ ID NO:23).

In general, the peptides hereinabove described are ion channel-forming peptides.

An ion channel-forming peptide or ionophore is a peptide which increases the permeability for ions across a natural or synthetic lipid membrane. B. Christensen et al., *PNAS*, Vol. 85 Pgs. 5072–76 (July, 1988) and Anzai, et al., *Biochimica et Biophysica Acta.*, Vol. 1064, pgs. 256–266 (1991), describe methodology which indicates whether or not a peptide has ion channel-forming properties and is therefore an ionophore. As used herein an ion channel-forming peptide is a peptide which has ion channel-forming properties as determined by the method of Christensen, et al. or Anzai, et al.

In one embodiment, the hereinabove described peptides may be acetylated with a $CH_3CO$—group at the N-terminal, said $CH_3CO$—group being hereinafter referred to by the letter X.

In another embodiment, the hereinabove described peptides may include an octanoyl group at the N-terminal.

In accordance with one embodiment, each of the amino acid residues contained in the peptides which is not glycine, is a D-amino acid residue. Although the scope of this particular embodiment is not to be limited to any theoretical reasoning, it is believed that the above-mentioned peptides, when consisting entirely of D-amino acid or glycine residues, may have increased resistance to proteolytic enzymes while retaining their biological activity. Such peptides thus may be administered orally. Also, in accordance with another embodiment, all of the amino acid residues may be D-amino acid or glycine residues, or L-amino acid or glycine residues.

In general, the peptides and/or analogues or derivatives thereof are generally water soluble to a concentration of at least 20 mg/ml at neutral pH in water. In addition, the structure of such peptides provides for flexibility of the peptide molecule. When the peptide is placed in water, it does not assume an amphiphilic structure. When the peptide encounters an oily surface or membrane, the peptide chain folds upon itself into a rod-like structure.

The peptides and/or analogues or derivatives thereof may be administered to a host; for example a human or non-human animal, in an amount effective to inhibit growth of a target cell, virus, or virally-infected cell. Thus, for example, the peptides and/or analogues or derivatives thereof may be used as antimicrobial agents, anti-viral agents, anti-bacterial agents, anti-tumor agents, anti-parasitic agents, spermicides, as well as exhibiting other bioactive functions.

The term "antimicrobial" as used herein means that the polypeptides of the present invention inhibit, prevent, or destroy the growth or proliferation of microbes such as bacteria, fungi, viruses, or the like.

The term "anti-bacterial" as used herein means that the polypeptides employed in the present invention produce effects adverse to the normal biological functions of bacteria, including death or destruction and prevention of the growth or proliferation of the bacteria when contacted with the polypeptides.

The term "antibiotic" as used herein means that the peptides employed in the present invention produce effects adverse to the normal biological functions of the non-host cell, tissue or organism, including death or destruction and prevention of the growth or proliferation of the non-host cell, tissue, or organism when contacted with the peptides.

The term "spermicidal" as used herein means that the polypeptides employed in the present invention, inhibit, prevent, or destroy the motility of sperm.

The term "antiviral" as used herein means that the polypeptides employed in the present invention inhibit, prevent, or destroy the growth or proliferation of viruses, or of virally-infected cells.

The term "anti-tumor" as used herein means that the polypeptide inhibits the growth of or destroys tumors, including cancerous tumors.

The term "anti-parasitic" as used herein means that the polypeptides employed in the present invention inhibit, prevent, or destroy the growth or proliferation of parasites.

The peptides of the present invention have a broad range of potent antibiotic activity against a plurality of microorganisms including gram-positive and gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic, antimicrobial, antiviral, and antibacterial properties of the peptides, they may also be used as preservatives or sterilants or disinfectants of materials susceptible to microbial or viral contamination.

The peptides and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptides of the present invention may be administered to a host; in particular a human or non-human animal, in an effective antibiotic and/or anti-tumor and/or anti-viral and/or anti-microbial and/or antibacterial and/or anti-parasitic and/or an antispermicidal amount.

Depending on the use, a composition in accordance with the invention will contain an effective anti-microbial amount and/or an effective antispermicidal amount and/or an effective anti-viral amount and/or an effective anti-tumor amount and/or an effective anti-parasitic and/or an effective antibiotic amount of one or more of the hereinabove described peptides which have such activity. The peptides may be administered by direct application of the peptides to the target cell or virus or virally-infected cell, or indirectly applied through systemic administration.

The peptides of the present invention may also be employed in promoting or stimulating healing of a wound in a host.

The term "wound healing" as used herein includes various aspects of the wound healing process.

These aspects include, but are limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to reverse the inhibition of wound healing caused by conditions which depress or compromise the immune system.

The peptides of the present invention may be used in the treatment of external burns and to treat and/or prevent skin and burn infections. In particular, the peptides may be used to treat skin and burn infections caused by organisms such as, but not limited to, *P. aeruginosa* and *S. aureus.*

The peptides are also useful in the prevention or treatment of eye infections. Such infections may be caused by bacteria such as, but not limited to, *P. aeruginosa, S. aureus,* and *N. gonorrhoeae,* by fungi such as but not limited to *C. albicans* and *A. fumigatus,* by parasites such as but not limited to *A. castellani,* or by viruses.

The peptides may also be effective in killing cysts, spores, or trophozoites of infection - causing organisms. Such organisms include, but are not limited to Acanthamoeba which forms trophozoites or cysts, *C. albicans,* which forms spores, and *A. fumigatus,* which forms spores as well.

The peptides may also be administered to plants in an effective antimicrobial or antiviral or antiparasitic amount to prevent or treat microbial or viral or parasitic contamination thereof.

The peptides, when used in topical compositions, are generally present in an amount of at least 0.1%, by weight. In most cases, it is not necessary to employ the peptide in an amount greater than 2.0%, by weight.

In employing such compositions systemically (intramuscular, intravenous, intraperitoneal), the active peptide is present in an amount to achieve a serum level of the peptide of at least about 5 µg/ml. In general, the serum level of peptide need not exceed 500 µg/ml. A preferred serum level is about 100 µg/ml. Such serum levels may be achieved by incorporating the peptide in a composition to be administered systemically at a dose of from 1 to about 10 mg/kg. In general, the peptide(s) need not be administered at a dose exceeding 100 mg/kg.

The peptides may be produced by known techniques and obtained in substantially pure form. For example, the peptides may be synthesized on an automatic peptide synthesizer. *Journal of the American Chemical Society*, Vol. 85, pgs. 2149–54 (1963). It is also possible to produce such peptides by genetic engineering techniques.

Thus, within the scope of the present invention there may be provided DNA which encodes the peptides hereinabove described. The codons for the amino acids which are included in the peptides are known to those skilled in the art. Therefore, one may construct DNA encoding the peptides by appropriate techniques, and place such DNA into an appropriate expression vehicle. Thus, one may administer the peptide by administering to a host cell transformed with an expression vehicle including DNA which encodes the peptide(s).

In accordance with another embodiment, the peptides of the present invention may be employed in combination with an ion having pharmacological properties for the purposes hereinabove described.

An ion having pharmacological properties is one which when introduced into a target cell, virus, or virally-infected cell, inhibits and/or prevents and/or destroys the growth of the target cell, virus, or virally-infected cell.

Such an ion having pharmacological properties is one which in the absence of an ion channel forming peptide is unable to cross a natural or synthetic lipid membrane; in particular a cell membrane, in sufficient amounts to affect a cell or virus adversely.

The peptide and ion having pharmacological properties may be administered as a single composition or in separate compositions, and the single or separate compositions may include additional materials, actives and/or inactives, in addition to the peptide and ion having pharmacological properties. As representative examples of ions having pharmacological properties which may be employed, there may be mentioned fluoride, peroxide, bicarbonate, silver, zinc, mercury, arsenic, copper, platinum, antimony, gold, thallium, nickel, selenium, bismuth, and cadmium ions.

The peptide and the ion having pharmacological properties, whether administered or prepared in a single composition or in separate compositions, are employed in amounts effective to inhibit and/or prevent and/or destroy the growth of the target cell. In effect, the ion potentiates the action of the peptide, i.e., the amount of ion is effective to reduce the maximum effective concentration of the peptide or protein for inhibiting growth of a target cell, virus, or virally-infected cell.

The ion having pharmacological properties, when used topically, is generally employed in a concentration of from 0.05% to 2.0%. When used systemically, the ion is generally employed in an amount of from 1 to 10 mg. per kg. of host weight. Peptide dosages may be within the ranges hereinabove described.

It is also to be understood that the peptide and ion having pharmacological properties, may be delivered or administered in different forms; for example, the toxic ion may be administered orally, while the peptide may be administered by IV or IP.

As representative examples of administering the peptide or protein and ion for topical or local administration, the peptide could be administered in an amount of up to about 1% weight to weight and the ion delivered in an amount of about 50 mM (about 0.1%). Alternatively, the ion, in the form of a salt such as sodium fluoride, could be administered orally in conjunction with systemic administration of the peptide. For example, the peptide may be administered IV or IP to achieve a serum dose of 100 micrograms per milliliter (10 milligrams per kilogram) in conjunction with an oral dose of ion, in particular, sodium fluoride, of 10 meq per kilogram.

In accordance with another embodiment, the peptides of the present invention may be administered to a host in combination with an antibiotic selected from the class consisting of bacitracins, gramacidin, polymyxin, vancomycin, teichoplanin, aminoglycosides, hydrophobic antibiotics, penicillins, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-O-methyl-1-4''-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-O-alpha-L-cladinosyl moiety, such as 3-O-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The peptide and antibiotic may be administered by direct administration to a target cell or by systemic or topical administration to a host which includes the target cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Peptide dosages may be those as hereinabove described.

As representative examples of administering the peptide and antibiotic for topical or local administration, the peptide could be administered in an amount of from about 0.1% to about 10% weight to weight, and the antibiotic is delivered in an amount of from about 0.1% to about 10% weight to weight.

In accordance with another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents, may also have anti-fungal activity, and that certain anti-fungal agents may have anti-parasitic activity.

In accordance with another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the peptides of the present invention may be administered for the purpose hereinabove described in combination with other biologically active amphiphilic peptides, or in combination with ion channel-forming proteins.

The present invention will be further described with respect to the following example; however, the scope of the invention is not to be limited thereby.

Example

Table I, which follows, indicates the Minimal Inhibitory Concentration (MIC) in $\mu$g/ml of Peptides (SEQ ID NO:1) through (SEQ ID NO:4), (SEQ ID NO:6) through (SEQ ID NO:13), (SEQ ID NO:16), (SEQ ID NO:20), (SEQ ID NO:21) and (SEQ ID NO:23) against S. aureus strain ATCC 25923, P. aeruginosa strain ATCC 27853, E. coli strain 25922, and Candida albicans.

The procedure for the antibacterial assay is based upon the guidelines of the National Committee for Clinical Laboratory Standards, Document M7-T2, Volume 8, No. 8, 1988.

Stock solutions of the peptides hereinabove mentioned are prepared at a concentration of 512 $\mu$g/ml in sterile deionized distilled water and stored at 31 70° C. Each peptide is a C-terminal amide and may or may not be acetylated at the N-terminus. An acetyl group at the N-terminus is indicated by an X.

The stock peptide solution is diluted in serial dilutions (1:2) down the wells of a microtiter plate so that the final concentrations of peptides in the wells are 0.25, 0.50, 1, 2, 4, 8, 16, 32, 64, 128, and 256 $\mu$g/ml. $1-5\times10^5$ CFUs/ml of either S. aureus ATCC 25923, E. coli ATCC 25922, P. aeruginosa ATCC 27853, or Candida albicans were added to the wells in full strength Mueller Hinton broth (BBL 11443) from a mid-log culture. The inoculum is standardized spectrophotometrically at 600 nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate. The minimal inhibitory concentration of each of the peptides hereinabove mentioned is given in Table I below.

TABLE I

| Peptide | Minimal Inhibitory Concentration ($\mu$g/ml) | | | |
|---|---|---|---|---|
| | S. aureus | P. aeruginosa | E. coli | C. albicans |
| X- (SEQ ID NO: 1)-NH$_2$ | 8 | 8, 16 | 8 | 128 |
| (SEQ ID NO: 2)-NH$_2$ | 4, 8 | 8 | 16 | n/a |
| (SEQ ID NO: 3)-NH$_2$ | 32 | 16 | 16, 32 | n/a |
| (SEQ ID NO: 4)-NH$_2$ | 16 | 4 | 4, 8 | 64 |
| (SEQ ID NO: 6)-NH$_2$ | 32 | 16 | 16 | n/a |
| (SEQ ID NO: 7)-NH$_2$ | 16 | 8 | 16 | n/a |
| (SEQ ID NO: 8)-NH$_2$ | 16 | 4 | 8, 16 | 64 |
| (SEQ ID NO: 9)-NH$_2$ | 64 | 8 | 8, 16 | 64, 128 |
| (SEQ ID NO: 10)-NH$_2$ | 16 | 4, 8 | 2, 4 | 64 |
| (SEQ ID NO: 11)-NH$_2$ | 64 | 8, 16 | 8, 16 | 64 |
| (SEQ ID NO: 12)-NH$_2$ | 8, 16 | 32 | 16, 32 | 128 |
| (SEQ ID NO: 13)-NH$_2$ | 32, 64 | 4 | 2, 4 | 64 |
| (SEQ ID NO: 16)-NH$_2$ | 4 | 2, 4 | 8 | 64 |
| (SEQ ID NO: 19)-NH$_2$ | 8 | 8 | 8, 16 | n/a |
| (SEQ ID NO: 20)-NH$_2$ | 8, 16 | 8, 16 | 4, 8 | 128 |

TABLE I-continued

| Peptide | Minimal Inhibitory Concentration (µg/ml) | | | |
|---|---|---|---|---|
| | S. aureus | P. aeruginosa | E. coli | C. albicans |
| (SEQ ID NO: 21)-NH$_2$ | 16 | 4 | 4 | 64 |
| (SEQ ID NO: 23)-NH$_2$ | 16 | 8, 16 | 32 | 128 |

The peptides of the present invention, whether administered alone or in combination with agents such as ions having pharmalogical properties, antibiotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline The peptides of the present invention, whether administered alone or in combination with agents such as ions having pharmalogical properties, antibiotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptide and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptide may be administered to a host in particular an animal, in an effective antibiotic and/or antitumor and/or antiviral and/or antimicrobial and/or antispermicidal and/or antifungal and/or antiparasitic amount, or in an amount effective to stimulate wound healing in a host. The peptides may be administered either alone or in combination with an ion having pharmacological properties, antibiotic, or ion channel forming peptide or protein as hereinabove described. When the peptide is administered in combination with a ion having pharmacological properties, the activity of the peptide is potentiated.

When the peptide is administered in combination with an agent as hereinabove described, it is possible to administer the peptide and agent in separate forms. For example, the agent may be administered systemically and the peptide may be administered topically.

When the peptide is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide may also be employed in combination with a ion having pharmacological properties, as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The peptide and toxic ion may be used to inhibit, prevent, or destroy the growth of *Streptococcus mutans*, which is associated with dental caries and periodontal disease.

Numerous modifications and variations of the present invention are possible in light of the above teachings; therefore, within the scope of the appended claims the invention may be practiced otherwise than as particularly described.

What is claimed is:

1. A peptide of the following structural formula:

Ile $R_1$ Lys Phe Leu Lys Lys Ala Lys Lys Phe
        5                   10

Gly Lys $R_2$ Phe $R_3$ Lys $R_4$ $R_5$ Lys Lys, wherein
        15              20

$R_1$ is Gly or Lys; $R_2$ is Ala or Lys; $R_3$ is Val or Lys; $R_4$ is Ile or Glu; and $R_5$ is Leu or Ile.

2. The peptide of claim 1 wherein said peptide has the following structural formula:

Ile Gly Lys Phe Leu Lys Lys Ala Lys Lys Phe
        5                   10

Gly Lys Ala Phe Val Lys Ile Leu Lys Lys.
        15              20

(SEQ ID NO: 1)

3. The peptide of claim 1 wherein said peptide has the following structural formula:

Ile Lys Lys Phe Leu Lys Lys Ala Lys Lys Phe
        5                   10

Gly Lys Lys Phe Lys Lys Ile Leu Lys Lys.
        15              20

(SEQ ID NO: 2)

4. The peptide of claim 1 wherein said peptide has the following structural formula:

Ile Gly Lys Phe Leu Lys Lys Ala Lys Lys Phe
        5                   10

Gly Lys Lys Phe Lys Lys Glu Ile Lys Lys.
        15              20

(SEQ ID NO: 3)

5. A peptide of the following structural formula:

Gly $R_1$ Gly Lys $R_2$ Leu Lys Lys Ala Lys Lys
        5                   10

$R_3$ Gly Lys Ala $R_4$ Val Lys $R_5$ Leu Lys Lys,
        15              20 wherein each of $R_1$, $R_2$, $R_3$, $R_4$, and $R_5$ is Ile or norleucine.

6. The peptide of claim 5 wherein each of $R_1$, $R_2$, $R_3$, $R_4$, and $R_5$ is Ile.

7. The peptide of claim 5 wherein each of $R_1$, $R_2$, $R_3$, $R_4$, and $R_5$ is norleucine.

8. A peptide of the following structural formula:

Gly Ile Gly Lys Phe Leu Lys Lys Ala Lys Lys
        5                   10

Phe Gly Lys Ala Phe Val Lys Ile R Lys Lys,
        15              20 wherein R is Val or norleucine.

9. The peptide of claim 8 wherein R is Val.
10. The peptide of claim 8 wherein R is norleucine.
11. A peptide of the following structural formula:

Gly Ile Gly Lys Phe Leu Lys Lys Ala Lys Lys
        5                   10

Phe Gly Lys Ala Phe Val Lys Ile Leu Lys Lys
        15              20

R, wherein R is Arg, Asn, or homoserine.

12. The peptide of claim 11 wherein R is Arg.
13. The peptide of claim 11 wherein R is homoserine.
14. The peptide of claim 11 wherein R is Asn.
15. A peptide of the following structural formula:

$R_1$ Gly Ile Gly Lys Phe Leu Lys Lys Ala Lys
        5                   10

Lys Phe Gly Lys Ala Phe Val Lys Ile Leu Lys
        15              20

Lys, wherein $R_1$ is Met or Arg.

16. A peptide of the following structural formula:

$R_1$ $R_1$ Gly Ile Gly Lys Phe Leu Lys Lys Ala
        5                   10

Lys Lys Phe Gly Lys Ala Phe Val Lys
        15              20

Ile Leu Lys Lys, wherein $R_1$ is Met or Arg.

17. A peptide of the following structural formula:

$R_1$ $R_1$ Gly Ile Gly Lys Phe Leu Lys Lys
        5                   10

Ala Lys Lys Phe Gly Lys Ala Phe Val Lys
        15              20

Ile Leu Lys Lys $R_2$, wherein $R_1$ is
                25

Met or Arg, and $R_2$ is a hydrophobic amino acid.

18. The peptide of claim 17 wherein $R_2$ is Gly.
19. A peptide of the following structural formula:

Gly Ile Gly Lys Phe Leu Lys Lys Ala Lys
        5                   10

Lys Phe Gly Lys Ala Phe Val Lys Ile Leu
        15              20

-continued

Lys Lys, wherein at least one of amino acid residues 15, 21, and 22 is a D-amino acid residue.

20. A peptide having the following structural formula:

Gly Ile Gly Lys Phe Leu Lys Lys Ala Lys Lys
                5                        10

Phe Gly Lys Ala Phe Val Lys Ile Leu
            15                  20

Lys Lys $R_1$ $R_2$, wherein $R_1$ is Asp or Ile, and $R_2$ is Asp or Glu.

21. A peptide of the following structure:

Gly Ile Gly Lys Phe Leu Lys Lys Ala Lys Lys Phe
                5                        10

Gly Lys Ala Phe Val Lys Ile Leu Lys Lys
            15                  20

$R_1$ $R_2$ $R_3$, wherein $R_1$ is Asp or Ile, $R_2$ is Asp or Glu, and $R_3$ is a hydrophobic amino acid or a basic hydrophilic amino acid.

22. A peptide of the following structure:

Gly Ile Gly Lys Phe Leu Lys Lys Ala Lys Lys
                5                        10

Phe Gly Lys Ala Phe Val Lys Ile Leu Lys Lys
            15                        20

$R_1$ $R_2$ $R_3$ $R_4$, wherein $R_1$ is Asp or Ile, $R_2$ is Asp or Glu, $R_3$ is a hydrophilic amino acid or a basic hydrophilic amino acid, and $R_4$ is a basic hydrophilic amino acid.

23. A peptide selected from the group consisting of:
(SEQ ID NO:16)
(SEQ ID NO:17)
(SEQ ID NO:18)
(SEQ ID NO:19)
(SEQ ID NO:20)
(SEQ ID NO:21)
(SEQ ID NO:22); and
(SEQ ID NO:23).

24. The peptide of claim 23 wherein said peptide has the following structural formula:
(SEQ ID NO:16).

25. The peptide of claim 23 wherein said peptide has the following structural formula:
(SEQ ID NO:17).

26. The peptide of claim 23 wherein said peptide has the following structural formula:
(SEQ ID NO:18).

27. A process for inhibiting the growth of a target cell, virus, or virally-infected cell in a host, comprising: administering to a host the peptide of claim 1, said peptide being administered in an amount effective to inhibit growth of a target cell, virus, or virally-infected cell in a host.

28. A process for inhibiting the growth of a target cell, virus, or virally-infected cell in a host, comprising: administering to a host the peptide of claim 5, said peptide being administered in an amount effective to inhibit growth of a target cell, virus, or virally-infected cell in a host.

29. A process for inhibiting the growth of a target cell, virus, or virally-infected cell in a host, comprising: administering to a host the peptide of claim 8, said peptide being administered in an amount effective to inhibit growth of a target cell, virus, or virally-infected cell in a host.

30. A process for inhibiting the growth of a target cell, virus, or virally-infected cell in a host, comprising: administering to a host the peptide of claim 11, said peptide being administered in an amount effective to inhibit growth of a target cell, virus, or virally-infected cell in a host.

31. A process for inhibiting the growth of a target cell, virus, or virally-infected cell in a host, comprising: administering to a host the peptide of claim 15, said peptide being administered in an amount effective to inhibit growth of a target cell, virus, or virally-infected cell in a host.

32. A process for inhibiting the growth of a target cell, virus, or virally-infected cell in a host, comprising: administering to a host the peptide of claim 19, said peptide being administered in an amount effective to inhibit growth of a target cell, virus, or virally-infected cell in a host.

33. A process for inhibiting the growth of a target cell, virus, or virally-infected cell in a host, comprising: administering to a host the peptide of claim 20, said peptide being administered in an amount effective to inhibit growth of a target cell, virus, or virally-infected cell in a host.

34. A process for inhibiting the growth of a target cell, virus, or virally-infected cell in a host, comprising: administering to a host the peptide of claim 23, said peptide being administered in an amount effective to inhibit growth of a target cell, virus, or virally-infected cell in a host.

35. A process for inhibiting the growth of a target cell, virus or virally-infected cell in a host, comprising: administering to a host the peptide of claim 16, said peptide being administered in an amount effective to inhibit growth of a target cell, virus, or virally-infected cell in a host.

36. A process for inhibiting the growth of a target cell, virus, or virally-infected cell in a host, comprising: administering to a host the peptide of claim 17, said peptide being administered in an amount effective to inhibit growth of a target cell, virus, or virally-infected cell in a host.

37. A process for inhibiting the growth of a target cell, virus, virally-infected cell in a host, comprising: administering to a host the peptide of claim 21, said peptide being administered in an amount effective to inhibit growth of a target cell, virus, virally-infected cell in a host.

38. A process for inhibiting the growth of a target cell, virus, virally-infected cell in a host, comprising: administering to a host the peptide of claim 22, said peptide being administered in an amount effective to inhibit growth of a target cell, virus, or virally-infected cell in a host.

* * * * *

UNITED STATES PATENT AND TRADEMARK OFFICE
CERTIFICATE OF CORRECTION

PATENT NO. : 5,424,290
DATED : June 13, 1995
INVENTOR(S) : W. Lee Maloy and U. Prasad Kari It is certified that error appears in the above-indentified patent and that said Letters Patent is hereby corrected as shown below:

Claim 20, col. 27, line 14, change "$R_2$is" to --$R_2$ is--.

Claim 28, col. 27, line 61, change "vitally-infected" to --virally-infected--.

Claim 37, col. 28, line 52, change "vitally-infected" to --virally-infected--.

Signed and Sealed this

Twenty-second Day of August, 1995

Attest:

BRUCE LEHMAN

Attesting Officer

Commissioner of Patents and Trademarks